United States Patent [19]
Gilbert et al.

[11] 4,421,741
[45] Dec. 20, 1983

[54] PHARMACEUTICAL COMPOSITIONS

[75] Inventors: David J. Gilbert, Bishops Stortford; Derek A. Hollingsbee, Chelmsford, both of England

[73] Assignee: Smith and Nephew Associated Companies Limited, England

[21] Appl. No.: 386,745

[22] Filed: Jun. 9, 1982

Related U.S. Application Data

[62] Division of Ser. No. 253,184, Apr. 13, 1981, Pat. No. 4,349,563.

[30] Foreign Application Priority Data

Apr. 18, 1980 [GB] United Kingdom ................ 8012853

[51] Int. Cl.³ .................... A61K 31/40; A61K 31/70; A61K 31/71; A61K 37/00
[52] U.S. Cl. ................................ 424/104; 424/180; 424/181; 424/274
[58] Field of Search ............... 424/274, 177, 180, 181

[56] References Cited

PUBLICATIONS

Merck Index, 9th Ed. (1976), p. 1224.

Primary Examiner—Stanley J. Friedman
Attorney, Agent, or Firm—Jacobs & Jacobs

[57] ABSTRACT

An anti-inflammatory pharmaceutical composition is described which is adapted for topical application to the eye and contains as active principle a compound of formula

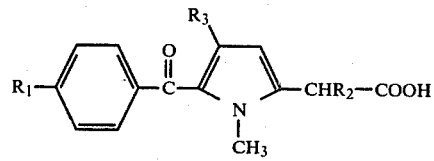

or a pharmaceutically acceptable salt thereof where $R_1$ is a chlorine atom or a methyl group, $R_2$ is a hydrogen atom or a methyl group and $R_3$ is a hydrogen atom or a methyl group. The composition may be used to treat ocular inflammation.

104 Claims, No Drawings

PHARMACEUTICAL COMPOSITIONS

CROSS-REFERENCE

This is a division of Ser. No. 253,184 filed Apr. 13, 1981 now U.S. Pat. No. 4,349,563.

The present invention relates to a pharmaceutical composition, its preparation and use. More specifically this invention relates to an anti-inflammatory ophthalmic composition comprising as active principle an arylacetic acid or a pharmaceutically acceptable salt thereof and to the preparation and use of such compositions.

Steroidal anti-inflammatory agents are well known which are effective in controlling inflammation in the eye. However the use of steroids may give rise to undesirable side-effects such as the masking or enhancement of corneal infections or cause elevation of intraocular pressure, so that for certain ophthalmic compositions some authorities would prefer to employ a non-steroidal anti-inflammatory agent.

Whilst a large number of non-steroidal anti-inflammatory agents including arylacetic acids and their salts are known to be effective in the treatment of inflammatory conditions such as arthritis when administered systemically it has been found that such agents in general have little or no effectiveness when applied topically to the eye, for example, in the form of eye drops. In our experience there is no correlation between known systemic anti-inflammatory activity and anti-inflammatory effectiveness in the eye. It has therefore been impossible to predict whether a given non-steroidal anti-inflammatory agent would be effective in the eye or not. In fact so far no arylacetic acid has found clinical use for topical administration in the eye.

Clearly it is desirable to provide a composition which may be administered to the eye to reduce inflammation and which does not depend for its effectiveness on the presence of a steroid.

A class of non-steroidal anti-inflammatory arylacetic acids is disclosed in U.S. Pat. No. 3,752,826 (see also British Pat. No. 1,195,628). Whilst the pharmaceutical use of the 5-benzoyl pyrolle alkanoic acids in the systemic treatment of rheumatoid arthritis and analgesia was described, no suggestion of the desirability of ophthalmic application was made.

The present invention provides an anti-inflammatory ophthalmic composition comprising as active principle a compound of formula (I):

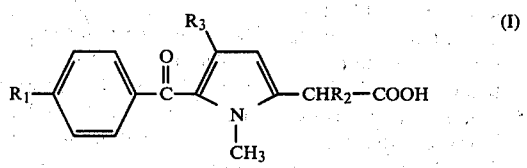

or a pharmaceutically acceptable salt thereof wherein $R_1$ is a chlorine atom or a methyl group, $R_2$ is a hydrogen atom or a methyl group and $R_3$ is a hydrogen atom or a methyl group. This adaption of such compositions for topical administration to the eye is surprising.

Particularly suitable compounds of the formula (I) are 5-(p-methylbenzoyl)-1-methylpyrrole-2-acetic acid (that is the compound where $R_1$ is a methyl group and $R_2$ and $R_3$ are both hydrogen atoms) hereinafter known as "tolmetin" and 5-(p-chlorobenzoyl)-1,4 dimethylpyrrole-2-acetic acid (that is the compound where $R_1$ is a chlorine atom, $R_2$ is a hydrogen atom and $R_3$ is a methyl group) hereinafter known as 'zomepirac'. Of these compounds tolmetin is much preferred. Most suitably the compound of the formula (I) is in the form of a salt suitable for ocular administration.

The composition of this invention is preferably presented as a clear, sterile aqueous solution with the active principle present as a water-soluble salt. Particularly apt salts include the sodium or potassium salt of which the sodium salt is preferred.

From the foregoing it will be realised that highly favoured active principles for use in the compositions of this invention are the sodium and potassium salts of tolmetin and zomepirac and that the preferred active principle is the sodium salt of tolmetin.

Most suitably the composition of this invention will contain from 0.1–10% of the active principle as hereinbefore described, more favourably from 0.4–7% of said active principle and preferably 0.5–5%, for example 1–2% or 2–5% of said active principle, (% terms when used herein are expressed on a wt/wt basis). Surprisingly clear aqueous solutions containing such levels of the active principle can be prepared and are stable to sterilisation techniques so that it is possible to provide the compositions of this invention in sterile form which is of great desirability.

In general compositions containing low levels of the active principle will require the presence of tonicity adjusting agents to bring the tonicity of the solution within the prescribed ranges. Most suitably the composition of this invention is rendered substantially isotonic, that is to say in terms of sodium chloride equivalent from 0.4 to 1.8% and more suitably from 0.6 to 1.5%. An isotonic solution has a sodium chloride equivalent of 0.9%. A discussion of isotonicity, sodium chloride equivalent and a list of tonicity agents is given in Remingtons' Pharmaceutical Sciences, Fifteenth Edition, p. 1405–1412.

Aptly the compositions of this invention will contain an antioxidant. Suitable antioxidants for use in this invention include citrate salts, N-acetyl cysteine, sodium thiosulphate, sodium metabisulphate and thiourea. A preferred antioxidant is trisodium citrate.

Suitably the antioxidant is present in an amount from 0.01 to 2.5%, preferably 0.05 to 2% and more preferably is 0.5 to 1.5% for example 1%.

Aptly the compositions of this invention will contain a metal ion sequestering agent. Suitable metal ion sequestering agents for use in this invention include sodium citrate, 8-hydroxyquinoline and its salts and ethylenediamine tetraacetic acid and its salts for example the disodium salt. A preferred antioxidant is trisodium citrate.

Suitably the sequestering agent is present in an amount from 0.001 to 2% and more preferably is from 0.5 to 1.5%.

From the aforementioned it is clear that an anti-oxidant and a metal ion sequestering agent may be used in combination. A preferred agent which possesses both properties is trisodium citrate. The presence of for example sodium citrate has been found to reduce the tendency of the compositions to discolour on storage by oxidation which may be catalysed by metal ions such as those of group IIa, Ib, IIb and IVb of the periodic table and in particular copper, ferrous and ferric ions. Secondly the presence of for example trisdium citrate as a sequestering agent has been found to prevent the precipitation of insoluble tolmetin salts of the metal ions described above and in particular with calcium ions which may leach from a glass bottle.

Optionally compositions of this invention may be buffered to a pH value of from 6.0 to 8.6. For solution at the higher value of pH for example 8.5 the preferred buffering system is a mixture of sodium borate and boric acid. At the preferred values of 7.0 to 8.0 the preferred buffering agents are a mixture of the alkali metal salts of orthophosphoric acid. However the addition of a buffering system to the composition may introduce inadvertently deleterious metal ions as described above and thereby require more chelating agent present.

Compositions of the present invention may be prepared advantageously without the presence of a buffer to have a pH value of 6.0 to 8.6 and more preferably from 7.0 to 8.0 for example 7.5.

Optionally the compositions of this invention will contain a stabilizer such as a surface active agent for example polyoxyethylene sorbitan fatty acid esters (commonly called Tween) or polyoxypropylene-polyoxyethylene diol block copolymers (commonly called Pluronic). A preferred stabiliser is polyoxyethylene sorbitan monooleate, Tween 80. The presence of a stabiliser is not preferred.

Normally the compositions of the invention will contain a preservative such as a phenylmercuric salt of nitric, boric or acetic acid or a quaternary ammonium compound such as benzalkonium chloride or chlorbutanol or thiomersal, the sodium salt of O-carboxyphenyl thioethyl mercury or phenylethanol or phenoxyethanol, including combinations of thiomersal with phenylethanol or benzalkonium chloride and combinations of phenylmercuric nitrate with phenylethanol or phenoxyethanol.

Preferred preservatives include a combination of thiomersal with phenylethanol and thiomersal with phenoxyethanol. A particularly preferred preservative is a combination of from 0.1 to 1% phenylethanol with 0.001 to 0.025% thiomersal, a most preferred combination is 0.5% phenylethanol and 0.01% thiomersal.

The particularly favoured form of the composition of the present invention comprises from 0.5 to 5.0% of the sodium salt of tolmetin, from 0.05 to 2% of trisodium citrate, 0.1 to 1% phenylethanol, 0.001 to 0.025% thiomersal in aqueous solution at a pH value of 7.0 to 8.0.

The preferred form of the composition of the present invention comprises from 1 to 2% of the sodium salt of tolmetin, 1% of trisodium citrate, 0.5% phenylethanol, 0.01% thiomersal in aqueous solution at a pH value of 7.5.

In a further particularly favoured form of the composition of the present invention an aminoglycoside or salt thereof may be present as an antibacterial. Aminoglycosides which may be used include neomycin, gentamycin, framycetin, polymixin B, tobramycin, kanamycin, vancomycin, amikacin and their salts include sulphate and phosphate. Suitably the aminoglycoside or its salt is present in an amount from 0.1 to 3.0%, more favourably from 0.2 to 1% and preferably 0.5%.

In a preferred form of the composition of the present invention, the antibacterial agent is neomycin or one of its salts, particularly aptly neomycin sulphate.

However, in aqueous solution in the absence of a soubilising agent at a pH value of below 8.5 and more rapidly at a pH value of below 8 the neomycin cation has been found to form with the tolmetin anion an insoluble product. To prevent the insoluble product being precipitated from solution, a solubilising agent is preferably added. This agent contains for example an anion selected from phosphate, citrate, glycerophosphate, sulphate, tartrate or borate.

The orthophosphate anion is particularly effective in solubilising neomycin when present in the form of disodium hydrogen orthophosphate or dipotassium hydrogen orthophosphate. Such salts as phosphate may be produced in situ by the addition of suitable amounts of sodium or potassium phosphate and phosphoric acid. However it is preferred that citrate salts are used to aid in the solubilisation of neomycin. The most preferred citrate salt being trisodium citrate. The amount of solubilising anion used depends upon the weight of neomycin present. In general a weight ratio of solubilising anion to neomycin sulphate of 1:1 to 8:1, preferably 2:1 to 3:1 is used.

Alternatively, polyvinyl pyrrolidone may be used instead of the solubilising anion to maintain the active principles in solution. The amount of polyvinyl pyrrolidone present may be from 1 to 20%, particularly from 5 to 15%.

A further particularly favoured form of the composition of the present invention comprises from 0.4 to 7% of the sodium salt of tolmetin, from 0.2 to 1% of neomycin sulphate, 0.05 to 2% trisodium citrate, 0.1 to 1% phenyl ethanol, 0.001 to 0.025% thiomersal in an aqueous solution at a pH value of 7.0 to 8.0.

The preferred form of the composition of the present invention comprises 2 to 5% of the sodium salt of tolmetin, 0.5% neomycin sulphate, 1 to 2% trisodium citrate, 0.5% phenyl ethanol. 0.01% thiomersal in an aqueous solution at a pH value of 7.5.

A further preferred form of the composition of the present invention comprises 2 to 5% of the sodium salt of tolmetin, 0.5% of neomycin sulphate, 10% polyvinyl pyrrolidone, 0.5% phenylethanol, 0.01% thiomersal in an aqueous solution at a pH value of 7.5.

A further favourable composition of the present invention will contain as preferred antibacterial chloramphenicol in an amount from 0.1 to 3%. Compositions containing chloramphenicol will normally also contain a solubilising agent for chloramphenicol. Solubilising agents for chloramphenicol include sodium borate, polyvinyl alcohol and polyvinyl pyrrolidone. A preferred solubilising agent is polyvinyl pyrrolidone having a number average molecular weight of 40,000. This polyvinyl pyrrolidone is known as Plasdone C-30 (Registered trade mark of GAF Corp.). The amount of polyvinyl pyrrolidone present may be from 1 to 20%, particularly from 5 to 15%.

A further particularly favoured form of the composition of the invention contains from 4.0 to 7% of the sodium salt of tolmetin, from 0.1 to 3.0% chloramphenicol, 5 to 15% polyvinyl pyrrolidone, 0.05 to 2% trisodium citrate, 0.1 to 1.0% phenylethanol, 0.0025 to 0.025% thiomersal in an aqueous solution having a pH value of 7.5.

A further preferred form of the composition of the invention contains from 2 to 5% of the sodium salt of tolmetin, 0.5% chloramphenicol, 10% polyvinyl pyrrolidone, 0.5 to 1.5% trisodium citrate, 0.5% phenylethanol, 0.01% thiomersal in an aqueous solution having a pH of 7.5.

Generally the compositions of the present invention will be formulated for either a single or multi-dose pack. In single dosage form a suitable dose of the composition may be contained in a single capsule equipped to deliver drops of solution. In this presentation each capsule will hold from 0.3 to 0.7 ml. and will have been sterilised e.g. by autoclaving. More usually the composition will be provided as a multi-dose pack such as neutral glass eye drop bottle with a polypropylene screw cap containing from 5 to 15 ml., usually 6 to 10 ml., for example 7.5 ml. In manufacture sterile bottles or capsules may be filled aseptically with a solution sterilised by filtration. Alternatively the bottle or capsule may be filled, sealed and the bottle or capsule and its contents sterilised by heat, for example by autoclaving. The concentration of the active ingredient in the composition is so adjusted that each drop delivers a suitable dose for example 0.2 to 5 mg. of for example the sodium salt of tolmetin. Generally a drop will contain from 20 to 50 microliters of solution. The indications for use include pre- and post-operative inflammations, uveitis and conjunctivitis. Administration of the drops will range from hourly to 3 times a day. At each application usually 1 to 2 drops will be given.

In a preferred embodiment the invention provides a clear sterile aqueous solution comprising the sodium salt of tolmetin and neomycin sulphate or chloramphenicol, a solubiliser, an antioxidant, a sequestering agent and a preservative combination in a multi-dose container provided with a dropper adapted to provide 0.2 to 5 mg., more usually 1 to 2 mg, of the sodium salt of tolmetin in 1 to 5 drops of 20 to 50 microliters and preferably in 1 to 2 drops of solution.

The invention also embraces a single sterile drop of the said composition in liquid form comprising from 1 to 2 mg of the sodium salt of tolmetin.

Such a dosage is clearly distinguished from a dosage formulated for systemic use, which may typically comprise from 100 to 200 mg of the sodium salt of tolmetin and is not in sterile form.

In further preferred compositions of the present invention the active principle is contained in an emulsion. Preferred emulsions are those which are of the water-in-oil type, whereby the oil is the continuous phase and the aqueous phase is dispersed in it.

Suitably the emulsion will contain from 1 to 10% of the active principle, more suitably 0.5 to 5% and preferably from 2 to 5%. The active principle is suitably tolmetin or the sodium salt of tolmetin. Preferably the active principle is the sodium salt of tolmetin.

Suitably the emulsion will contain a sequestering agent or antioxidant as hereinbefore described. Particularly suitable sequestering agents or antioxidants are the salts of citric acid. Preferably the sequestering agent or antioxidant is trisodium citrate. Suitably the sequestering agent or antioxidant is present in an amount from 0.01 to 2.0%, more suitably 0.075 to 1.5% and preferably from 0.1 to 0.5%.

Normally any pharmacologically acceptable oil may be used in the emulsions of the present invention. Suitably these oils include vegetable and mineral oils such as castor oil, liquid paraffin, white soft paraffin including mixtures thereof. Suitably the oil phase will contain a mixture of liquid paraffin and white soft paraffin and preferably will contain a mixture of liquid paraffin, white soft paraffin and castor oil. Suitably the oil phase is present in an amount from 40 to 65% and preferably from 45 to 60%.

Conventionally the emulsion of the present invention will contain one or more emulsifying agents. Suitable emulsifying agents include glyceryl monoisostearate, ceto stearyl alcohol, hydrogenated castor oil and sorbitan sesquioleate and including mixtures thereof. Preferred emulsifying agents are glyceryl monoisostearate and glyceryl monoisostearate together with sorbitan sesquioleate and hydrogenated castor oil. Suitably the emulsifying agent is present in an amount from 1 to 20%, more suitably from 2.5 to 10%.

Suitably the emulsions of the present invention will contain a preservative. Suitable preservatives include chlorbutanol, chlorocresol, benzalkonium chloride, thiomersal, phenylethanol, phenoxyethanol and mixtures thereof. A particularly preferred preservative is phenylethanol. Suitably the preservative is present in an amount from 0.1 to 1% and preferably is 0.5%.

A suitable form of the emulsion of this invention contains 0.5 to 5% of the sodium salt of tolmetin, 0.1 to 0.5% of trisodium citrate, 0.5% phenylethanol, 5.0% glyceryl monoisostearate, 27.5% of liquid paraffin, 20.0% of white soft paraffin, 10.0% of hydrogenated castor oil and 34.9% of water.

A preferred form of the emulsion of this invention contains 2 to 5% of the sodium salt of tolmetin, 0.1 to 0.5% of trisodium citrate, 0.5% of phenylethanol, 3.0% of glyceryl monoisostearate, 26.5% of liquid paraffin, 20.0% of white soft paraffin, 10% of hydrogenated castor oil, 3% of sorbitan sesquioleate and 34.9% water.

A further preferred form of the composition is as a sterile ophthalmic ointment. Suitably the active principle is present as a compound of formula (I) or a pharmaceutically acceptable salt. Particularly suitable compounds are tolmetin or the sodium salt of tolmetin in either their anhydrous or hydrated forms. Particularly preferred is the anhydrous form of the sodium salt of tolmetin. When in this form the compound may be sterilised by gamma irradiation without discolouration. Suitably the active principle is present in an amount from 0.1 to 10% and preferably from 0.5 to 6%.

Ointment bases suitable for this invention include a mixture of white or yellow soft paraffin and liquid paraffin or the Eye Ointment Basis, comprising wool fat (1 part), liquid paraffin (1 part) and yellow soft paraffin (8 parts), described in the Pharmaceutical Codex 1979 11th Edition p 349. Preferred ointment bases include a mixture of white soft paraffin and liquid paraffin in a ratio of 1:0.80 to 1:1.

It is desirable that ophthalmic ointments are sterile, substantially free from foreign particulate contamination and the particle size of the active ingredient is reduced to impalpability. It is preferred to prepare and pack the ointment under aseptic conditions by bringing together pre-sterilised ingredients under sterile conditions. The ointment base may be sterilised by melting together the ingredients and filtering through an 0.22 micron filter. The sodium salt of tometin may be sterilised by dissolving the salt in water, filtering through a 0.22 micron filter and freeze-drying the sterile solution. The material may then be ground and micronised aseptically. It is preferred, however, to micronise the anhydrous sodium salt of tolmetin and then sterilise this solid by gamma irradiation at 2.5 Mrad.

For use in ointments of this invention it is preferred that the solid sodium salt of tolmetin is micronised that is to say 99% of the particles are smaller than 20 microns in diameter, 90% of the particles are below 10 microns. The majority of particles are in the range of 1 to 5 microns in diameter.

A short discussion on the desirable properties and preparation of sterile ophthalmic ointments is given in Remington's Pharmaceutical Sciences, Fifteenth Edition p. 1503–4.

The particular favoured form of the composition of the present invention comprises a sterile ointment containing from 0.5 to 6% of the anhydrous sodium salt of tolmetin and a mixture of white soft paraffin/liquid paraffin in a ratio from 1:0.8 to 1:1.

The preferred form of the composition of this invention comprises from 1 to 2% of the anhydrous sodium salt of tolmetin, 52.5% white soft paraffin and from 44.5 to 45.5% liquid paraffin.

In a further form of the present invention the ointment described hereinbefore may suitably contain an antibacterial agent such as an aminoglycoside or salt thereof or chloramphenicol in an amount from 0.1 to 3%.

A particularly favoured form of the composition of the present invention comprises 1 to 2% of the anydrous sodium salt of tolmetin, 0.5% neomycin sulphate, 52.25% white soft paraffin and from 45.25% to 46.25% liquid paraffin.

Alternatively a second favoured form of the composition comprises 1 to 2% of the anhydrous sodium salt of tolmetin, 1.0% of chloramphenicol, 52.5% white soft paraffin and 44.5 to 45.5% liquid paraffin.

The present invention also envisages a method of treatment of the human or domestic mammal eye which comprises delivering thereto an anti-inflammatory composition of this invention.

In order to demonstrate the effectiveness of the anti-inflammatory compositions of the present invention, tests were carried out by the method given in "A detailed assessment procedure of anti-inflammatory effects of drugs on experimental immunogenic uveitis in rabbits". J. J. Ashford, J. W. Lamble in Investigative Ophthalmology 1974 13 (6) 414–421.

The effect of 1, 2 and 5% solutions of the sodium salt of tolmetin compared to vehicle treated eyes in rabbits with unilateral immune uveitis was measured using bolometry.

The rabbits were dosed with 50 microliters of the drug or vehicle applied topically to the lower conjunctival sac at zero, 2, 3, 6, 8 and 24 hours from the challenge. Representative measurements of corneal temperature were taken at 6, 24, 48 and 72 hours from the challenge.

| % sodium salt of tolmetin | 6 hours | 24 hours | 48 hours | 72 hours |
|---|---|---|---|---|
| 1% | −46 | −60 | +8 | +30 |
| 2% | −56 | −68 | −50 | +15 |
| 5% | −60 | −83 | −78 | −60 |

The table shows the mean percent reduction of a number of sodium salt of tolmetin solutions treated versus vehicle treated groups of the mean corneal temperature for various concentrations of sodium salt of tolmetin.

A private pilot study on the anti-inflammatory activity of the sodium salt of tolmetin versus a saline control was carried out in patients subsequent to cataract extraction. Eight patients received 50 microliters of a 5% aqueous solution of the sodium salt of tolmetin four times daily for a period of 36 days or until the remaining inflammatory changes were minimal. Seven patients received a similar amount of saline four times a day. Each patient also received 1% atropine topically once daily. Atropine causes pupil dilation thereby facilitating fundus examination and reduces the risk of fibrous strands adhering the iris to lens.

By scoring signs and symptoms of inflammation, a noticeable improvement in these patients receiving the sodium salt of tolmetin was seen at day +8 post-operation, a definite improvement was seen at day +15 and by day +22 the difference in the two groups was statistically highly significant.

EXAMPLE 1

Sodium salt of tolmetin formulations

A formulation was prepared containing,

| | |
|---|---|
| Tolmetin sodium dihydrate | 2.0 g |
| Trisodium citrate | 1.0 g |
| Boric acid | 0.1 g |
| Phenylmercuric nitrate | 0.002 g |
| Sodium borate, 5% solution to adjust pH to 8.5 | |
| Distilled water to make volume up to 100 ml. | |

The solution was prepared by dissolving phenylmercuric nitrate in approximately 25 ml. of distilled water at room temperature with stirring. Trisodium citrate and boric acid were added and the solution stirred until both had completely dissolved. Then the sodium salt of tolmetin was dissolved in this solution. The pH of the solution was raised to 8.5 by addition of a 5% solution of sodium borate and the volume of the solution finally made up to 100 ml. with distilled water.

This solution was sterilised by filtration through a 0.22 micron filter from Millipore and packed in multi-dose sterile glass eye-dropper bottles.

Alternatively the solution may be placed in multi-dose glass eye-dropper bottles and the bottles and solution sterilised by autoclaving at 116° C. for 30 minutes.

EXAMPLE 2

Sodium salt of tolmetin formulation

A formulation was prepared containing:

| | |
|---|---|
| Tolmetin sodium dihydrate | 2.0 g |
| Trisodium citrate | 1.0 g |
| Boric acid | 0.1 g |
| Sodium borate 5% solution to adjust pH to 8.5 | |
| Distilled water to make up volume to 100 ml. | |
| Phenylmercuric nitrate | 0.002 g |

Trisodium citrate, boric acid and the sodium salt of tolmetin were sequentially dissolved in 40 ml. of distilled water, the pH of the solution was adjusted to 8.5 with a 5% solution of sodium borate and the volume of the solution was made up to 100 ml. with distilled water. 10 g. of a chelating resin, Chelex 100 Resin (of BioRad Laboratories, Richmond, Calif.) was added to this solution and the mixture stirred together for 30 minutes and the resin was then filtered off.

The phenylmercuric nitrate was dissolved in the filtrate. The pH and volume of the filtrate were readjusted to 8.5 and 100 ml.

The solution was then filled into the multi-dose eye-dropper bottles in a nitrogen atmosphere and sterilised by autoclaving at 116° C. for 30 minutes.

EXAMPLE 3

Sodium salt of tolmetin formulation

A formulation was prepared containing:

| | |
|---|---|
| Tolmetin sodium dihydrate | 2.0 g |
| Trisodium Citrate | 1.0 g |
| Boric Acid | 0.1 g |
| Sodium borate 5% solution to adjust pH to 8.5 | |
| Distilled water to make volume up to 100 ml. | |

The solution was prepared as in Examples 1 and 2. The solution was then filled into unit-dose packs and sterilised by autoclaving at 116° C. for 30 minutes.

EXAMPLE 4

Sodium salt of tolmetin—Chloramphenicol formulation

A formulation was prepared containing:

| | |
|---|---|
| Tolmetin sodium dihydrate | 5.0 g |
| Chloramphenicol | 0.5 g |
| Trisodium citrate | 1.5 g |
| Boric acid | 1.0 g |
| Sodium borate | 0.2 g |
| Polyvinyl alcohol, (GOHSENOL GH-17) | 3.5 g |
| Phenylmercuric nitrate | 0.002 g |
| Sodium hydroxide solution to adjust pH to 7.4 | |
| Distilled water to adjust volume to 100 ml. | |

The solution was prepared by dissolving phenylmercuric nitrate in 40 ml. of distilled water with stirring. Then the trisodium citrate, boric acid, sodium borate, polyvinyl alcohol and chloramphenicol were added and dissolved in solution. When all the aforementioned ingredients had completely dissolved, the sodium salt of tolmetin was added to the solution and dissolved with stirring. The pH of the resultant solution was then adjusted to a pH of 7.4 with sodium hydroxide solution and the volume made up to 100 ml. with distilled water.

The resultant solution was sterilised by filtration through a 0.22 micron filter and filled into sterile eye-dropper glass bottles.

EXAMPLE 5

Sodium salt of tolmetin—Chloramphenicol formulation

A formulation was prepared containing:

| | |
|---|---|
| Tolmetin sodium dihydrate | 1.0 g |
| Chloramphenicol | 0.5 g |
| Sodium borate | 0.3 g |
| Boric acid | 1.0 g |
| Polyoxyethylene sorbitan monooleate | 0.1 g |
| Phenylmercuric nitrate | 0.002 g |
| Benzalkonium chloride | 0.001 g |
| Sodium hydroxide solution to adjust pH to 7.4 | |
| Distilled water to adjust volume to 100 ml. | |

The solution was prepared, sterilised and packaged in the manner of Example 4.

EXAMPLE 6

Sodium salt of tolmetin—Neomycin sulphate formulation

A formulation was prepared containing:

| | |
|---|---|
| Tolmetin sodium dihydrate | 5.0 g |
| Trisodium citrate | 2.0 g |
| Neomycin sulphate | 0.5 g |
| Polyvinyl pyrrolidone | 10.0 g |
| Phenylmercuric nitrate | 0.002 g |
| Sodium hydroxide solution to adjust pH to 7.4 | |

| | |
|---|---|
| -continued | |
| Distilled water to make volume up to 100 ml. | |

The solution was prepared by dissolving the trisodium citrate and phenylmercuric nitrate in 50 ml. of distilled water at room temperature. The neomycin sulphate was added and dissolved in this solution. Polyvinyl pyrrolidone was added and the solution stirred to ensure all the ingredients had dissolved. The sodium salt of tolmetin was added and taken up into the solution.

The resultant solution was adjusted to a pH of 7.4 with sodium hydroxide and the volume of the solution then made up to 100 ml. with distilled water.

This solution was then sterilised and packaged in the manner of Example 4.

EXAMPLE 7

Sodium salt of tolmetin Ointment formulation

A formulation was prepared containing:

| | |
|---|---|
| Sodium tolmetin dihydrate | 5.0 g |
| White soft paraffin | 52.25 g |
| Liquid paraffin | 42.75 g |

The white soft paraffin and liquid paraffin were melted and mixed together to form a homogeneous fluid. This fluid was sterilised whilst hot by passing through a 0.22 micron filter and collected in a sterile mixing vessel.

The sodium salt of tolmetin was dissolved in 40 ml. of distilled water and filtered through a 0.22 micron filter. The filtrate was freeze dried under sterile conditions to give a sterile powder solid which has a particle size of less than 75 microns separated by sieving. The requisite amount of this fine powder was intimately mixed with the white soft paraffin/liquid paraffin mixture to give a sterile ophthalmically acceptable ointment containing the sodium salt of tolmetin.

The ointment was then packed in conventional ointment tubes under sterile conditions.

EXAMPLE 8

Sodium salt of tolmetin formulation

A formulation was prepared containing:

| | |
|---|---|
| Tolmetin sodium dihydrate | 2.0 g |
| Dipotassium hydrogen phosphate | 0.6 g |
| Potassium dihydrogen phosphate | 0.116 g |
| Polyvinyl alcohol (Gohsenol GL-05) | 3.0 g |
| Phenylmercuric nitrate | 0.002 g |
| Distilled water to adjust the volume to 100 ml. | |

This solution was then sterilised and packaged in the manner of Example 4.

EXAMPLE 9

Sodium salt of tolmetin—neomycin formulation

A formulation was prepared containing:

| | |
|---|---|
| Tolmetin sodium dihydrate | 5.0 g |
| Neomycin sulphate | 0.5 g |
| Disodium hydrogen phosphate | 1.0 g |
| Polyvinyl pyrrolidone | 10.0 g |
| Thiomersal | 0.02 g |
| Sodium hydroxide solution to adjust the pH to 7.4 | |

EXAMPLE 10

Sodium salt of tolmetin formulation

A formulation was prepared containing:

| | |
|---|---|
| Tolmetin sodium dihydrate | 5.0 g |
| Trisodium citrate | 1.0 g |
| Phenylmercuric nitrate | 0.002 g |
| Citric acid solution to adjust the pH to 7.5 | |
| Distilled water to adjust the volume to 100 ml. | |

This solution was then sterilised and packaged in the manner of Example 4.

EXAMPLE 11

Sodium salt of tolmetin ointment formulation

| | |
|---|---|
| Tolmetin sodium anhydrous (micronised) | 1.77% |
| White soft paraffin | 52.5% |
| Liquid paraffin to | 100 gm. |

The white soft paraffin and liquid paraffin were melted and mixed together to form a homogenous fluid. This fluid was sterilised by passing through a 0.22 micron cellulose ester bacterial filter and collected in a sterile mixing vessel.

The micronised anhydrous salt of tolmetin was sterilised by irradiation by gamma-rays at 2.5 Mrads. This sterile powder was intimately mixed with the white soft paraffin/liquid paraffin mixture under aseptic conditions to give a sterile ophthalmically acceptable ointment containing the sodium salt of tolmetin.

The ointment was then packed in conventional ointment tubes under sterile conditions.

EXAMPLE 12

Sodium salt of tolmetin/chloramphenicol ointment formulation

| | |
|---|---|
| Tolmetin sodium anhydrous (micronised) | 1.77% |
| Chloramphenicol (micronised) | 1.0% |
| White soft paraffin | 52.5% |
| Liquid paraffin to | 100 g. |

The ointment was prepared by the method described in Example 11, the micronised chloramphenicol being sterilised and added in a similar manner to the sodium salt of tolmetin.

EXAMPLES 13 AND 14

Sodium salt of tolmetin formulations

Formulations were prepared containing:

| | 13 | 14 |
|---|---|---|
| Tolmetin sodium dihydrate | 2.0% w/v | 5.0% w/v |
| Trisodium citrate | 1.0% w/v | 1.0% w/v |
| Phenylethanol | 0.5% w/v | 0.5% w/v |
| Thiomersal | 0.01% w/v | 0.01% w/v |
| Citric acid, 5% solution | adjust pH to 7.5 | adjust pH to 7.5 |
| Distilled water | to 100 ml. | to 100 ml. |

A solution was prepared by dissolving phenylethanol and thiomersal in distilled water (25 ml). The trisodium citrate was then added and the solution stirred until all the solid had dissolved. The sodium salt of tolmetin was then dissolved in this solution. The pH value of the solution was adjusted to 7.5 by the addition of 5% citric acid solution. The volume of the solution was finally raised to 100 ml by addition of distilled water.

This solution was sterilised by filtration through a 0.22 micron cellulose ester bacterial filter and aseptically filled into multidose sterile glass eye-dropper bottles.

EXAMPLES 15 AND 16

Sodium salt of tometin formulations

Formulations were prepared containing:

| | 15 | 16 |
|---|---|---|
| Tolmetin sodium dihydrate | 2.0% w/v | 5.0% w/v |
| Trisodium citrate | 1.0% w/v | 1.0% w/v |
| Citric acid 5% solution, | adjust pH to 7.5 | adjust pH to 7.5 |
| Distilled water | to 100 ml | to 100 ml. |

Solutions were prepared by dissolving the sodium citrate and sodium salt of tolmetin in distilled water (25 ml), adjusting the pH value to 7.5 with a 5% solution of citric acid and finally adjusting the volume to 100 ml with distilled water.

These solutions were then filled in to unit dose packs and sterilised by autoclaving at 116° C. for 30 minutes.

EXAMPLES 17 AND 18

Sodium salt of tolmetin—chloramphenicol formulation

Formulations were prepared containing:

| | 17 | 18 |
|---|---|---|
| Tolmetin sodium dihydrate | 2.0% w/v | 4.0% w/v |
| Chloramphenicol | 0.5% w/v | 0.5% w/v |
| Trisodium citrate | 1.0% w/v | 1.0% w/v |
| *Polyvinyl pyrrolidone (number average molecular wt. 40,000) | 10.0% w/v | 10.0% w/v |
| Thiomersal | 0.01% w/v | 0.01% w/v |
| Sodium hydroxide, 5% solution | to adjust pH to 7.5 | to adjust pH to 7.5 |
| Distilled water | to 100 ml | to 100 ml. |

*The polyvinyl pyrrolidone used was Plasdone C-30.

To prepare the solutions, the polyvinyl pyrrolidone, sodium citrate, thiomersal and chloramphenicol were added to distilled water (60 ml) and stirred until all the solid had dissolved. The sodium salt of tolmetin was then added and the solutions stirred until the solid had dissolved. The pH value of the solution was adjusted to 7.5 by addition of 5% sodium hydroxide solution. The volume of the solution was raised to 100 ml by addition of distilled water.

These solutions were sterilised by filtration through a 0.22 micron cellulose ester bacterial filter and aseptically filled into multidose sterile glass eye-dropper bottles.

EXAMPLES 19 AND 20

Sodium salt of tolmetin—chloramphenicol formulations

Formulations were prepared containing:

|  | 19 | 20 |
|---|---|---|
| Tolmetin sodium dihydrate | 2.0% w/v | 4.0% w/v |
| Chloramphenicol | 0.5% w/v | 0.5% w/v |
| Trisodium citrate | 1.0% w/v | 1.0% w/v |
| Polyvinyl pyrrolidone | 10.0% w/v | 10.0% w/v |
| Sodium hydroxide, 5% solution | to adjust pH to 7.5 | to adjust pH to 7.5 |
| Distilled water | to 100 ml | to 100 ml. |

The solutions were prepared as described for Examples 17 and 18.

The solutions were filled into unit-dose packs and sterilised by autoclaving at 100° C. for 30 minutes.

EXAMPLE 21, 22 AND 23

Sodium salt of tolmetin water-in-oil emulsion

Formulations of the sodium salt of tolmetin in the form of an emulsion (water-in-oil type) were prepared as follows:

|  | 21 | 22 | 23 |
|---|---|---|---|
| Tolmetin sodium dihydrate | 2.0% | 2.0% | 2.0% |
| Trisodium citrate | 0.1% | 0.1% | 0.1% |
| Phenylethanol | 0.5% | 0.5% | 0.5% |
| *Glyceryl monoisostearate | 5.0% | 5.0% | 3.0% |
| Water | 34.9% | 34.9% | 34.9% |
| Cetostearyl alcohol | 12.5% | — | — |
| Liquid paraffin | 22.5% | 27.5% | 26.5% |
| White soft paraffin | 22.5% | 20.0% | 20.0% |
| Hydrogenated castor oil | — | 10.0% | 10.0% |
| Sorbitan sesquioleate | — | — | 3.0% |

*Imwitor 780K, registered trademark of Dynamit Nobel.

The emulsions were prepared as follows. The sodium salt of tolmetin and trisodium citrate were dissolved in the water and the resultant solution heated to 75°–80° C. The remaining components, constituting the oil phase, were mixed together and heated to 80° C. with stirring to produce a homogenous oily liquid. Whilst maintaining the temperature and stirring the aqueous solution was added to the oily liquid and the emulsion so formed allowed to cool with stirring. The product was produced as a stable emulsion of the water-in-oil type.

What we claim is:

1. A method of treating ocular inflamation which comprises topically administering to the eye an anti-inflammatory amount of a composition which comprises an anti-inflammatory effective amount of a compound of the formula (I):

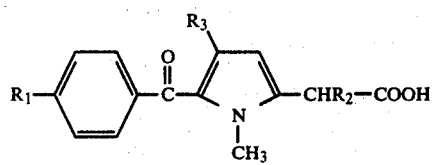

or a pharmaceutically acceptable salt thereof wherein $R_1$ is chloro or methyl; $R_2$ is hydrogen or methyl; and $R_3$ is hydrogen or methyl, and an antibacterially effective amount of an aminoglycoside selected from the group consisting of neomycin, gentamycin, framycetin, polymixin B, tobramycin, kanamycin, vancomycin and amikacin or a pharmaceutically acceptable salt thereof, in combination with an ocularly acceptable carrier.

2. A method according to claim 1 wherein the composition contains from 0.1 to 10% wt/wt of said compound in the form of a pharmaceutically acceptable salt.

3. A method according to claim 1 wherein the composition contains from 0.4 to 7% wt/wt of said compound in the form of a pharmaceutically acceptable salt.

4. A method according to claim 1 wherein the composition contains from 0.5 to 5% wt/wt of said compound in the form of a pharmaceutically acceptable salt.

5. A method according to claim 1 wherein the composition contains from 1 to 2% wt/wt of said compound in the form of a pharmaceutically acceptable salt.

6. A method according to claim 1 wherein the composition contains from 2 to 5% wt/wt of said compound in the form of a pharmaceutically acceptable salt.

7. A method according to claim 1 wherein the composition contains 2% wt of said compound in the form of a pharmaceutically acceptable salt.

8. A method according to claim 1 wherein the composition contains 5% wt of said compound in the form of a pharmaceutically acceptable salt.

9. A method according to claim 1 wherein the composition has been rendered substantially isotonic.

10. A method according to claim 1 wherein the composition contains from 0.01 to 2.5% of an antioxidant.

11. A method according to claim 1 wherein the composition contains from 0.05 to 2% of an antioxidant.

12. A method according to claim 1 wherein the composition contains from 0.5 to 1.5% of an antioxidant.

13. A method according to claim 1 wherein the composition contains 1% of an antioxidant.

14. A method according to claim 10 wherein the antioxidant is a citrate salt, N-acetylcysteine, sodium thiosulphate, sodium metabisulphate or thiourea.

15. A method according to claim 14 wherein the antioxidant is a citrate salt.

16. A method according to claim 15 wherein the citrate salt is trisodium citrate.

17. A method according to claim 1 wherein the composition contains from 0.001 to 2% of a metal ion sequestering agent.

18. A method according to claim 1 wherein the composition contains from 0.5 to 1.5% of a metal ion sequestering agent.

19. A method according to claim 18 wherein the composition also contains from 0.01 to 2.5% of an antioxidant.

20. A method according to claim 19 wherein the antioxidant and the metal ion sequestering agent is trisodium citrate.

21. A method according to claim 1 wherein the pH of the composition is 6.0 to 8.6.

22. A method according to claim 1 wherein the composition contains a preservative.

23. A method according to claim 22 wherein the preservative is phenylethanol and thiomersal.

24. A method according to claim 23 wherein the composition contains from 0.1 to 1% phenylethanol and from 0.001 to 0.025% thiomersal.

25. A method according to claim 1 wherein the compound is the sodium or potassium salt of tolemetin.

26. A method according to claim 1 wherein the compound is the sodium salt of tolemetin.

27. A method according to claim 26 wherein the composition is in the form of a clear, sterile aqueous solution.

28. A method according to claim 1 wherein the composition is in the form of a sterile emulsion.

29. A method according to claim 1 wherein the composition is in the form of a sterile ointment.

30. A method according to claim 1 wherein the composition is in the form of a clear, sterile, aqueous solution which comprises 0.5 to 2% wt/wt of the sodium salt of tolmetin, 0.1 to 3% of an aminoglycoside selected from the group consisting of meomycin, gentamycin, framycetin, polymixin B, tobramycin, kanamycin, vancomycin, amikacin or a pharmaceutically acceptable salt thereof, 0.5 to 2% of an antioxidant or sequestering agent and a preservative, the pH of said solution being from 7.0 to 8.0.

31. A method according to claim 30 wherein the antioxidant or sequestering agent is a citrate salt.

32. A method according to claim 31 wherein the citrate salt is trisodium citrate.

33. A method according to claim 32 wherein the preservative is a mixture of 0.5% phenylethanol and 0.01% thiomersal.

34. A method according to claim 1 when the aminoglycoside or pharmaceutically acceptable salt thereof is present in an amount of from 0.1% to 3.0%.

35. A method according to claim 1 when the aminoglycoside or pharmaceutically acceptable salt thereof is present in an amount of from 0.2% to 1%.

36. A method according to claim 1 when the aminoglycoside or pharmaceutically acceptable salt thereof is present in an amount of 0.5%.

37. A method according to claim 1 wherein the aminoglycoside is neomycin or a sulphate salt thereof.

38. A method according to claim 37 wherein the composition contains an amount of a solubilizing agent sufficient to prevent the neomycin cation from forming an insoluble precipitate with the anion of the compound of the formula (I).

39. A method according to claim 38 wherein the solubilizing agent contains an anion selected from the group consisting of phosphate, citrate, glycerophosphate, sulphate, tartrate and borate.

40. A method according to claim 38 wherein the compound of the formula (I) is in the form of the sodium salt of tolmetin, the aminoglycoside is neomycin or neomycin sulphate and the composition contains an amount of orthophosphate anion sufficient to prevent the neomycin cation from forming an insoluble precipitate with the tolmetin anion.

41. A method according to claim 40 wherein the orthophosphate anion is present in the form of disodium hydrogen orthophosphate or dipotassium hydrogen orthophosphate.

42. A method according to claim 39 wherein the weight ratio of solubilizing anion to neomycin sulphate is from 1:1 to 8:1.

43. A method according to claim 39 wherein the weight ratio of solubilizing anion to neomycin sulphate is from 2:1 to 3:1.

44. A method according to claim 38 wherein the solubilizing agent is polyvinyl pyrrolidone.

45. A method according to claim 44 wherein the polyvinyl pyrrolidone is present in an amount of from 1 to 20% by weight.

46. A method according to claim 44 wherein the polyvinyl pyrrolidone is present in an amount of from 5 to 15% by weight.

47. A method according to claim 1 wherein the composition comprises from 0.4% to 7% of the sodium salt of tolmetin, from 0.2% to 1% of neomycin sulphate, from 0.05 to 2% trisodium citrate, from 0.1 to 1% phenyl ethanol, and from 0.001 to 0.025% thiomersal in an aqueous solution at a pH of from 7.0 to 8.0.

48. A method according to claim 1 wherein the composition comprises from 2 to 5% of the sodium salt of tolmetin, 0.5% neomycin sulphate, 1 to 2% trisodium citrate, 0.5% phenyl ethanol, and 0.01% thiomersal in an aqueous solution at a pH of 7.5.

49. A method according to claim 1 wherein the composition comprises from 2 to 5% of the sodium salt of tolmetin, 0.5% neomycin sulphate, 10% polyvinyl pyrrolidone, 0.5% phenylethanol and 0.01% thiomersal in an aqueous solution having a pH of 7.5.

50. A method according to claim 38 wherein the solubilizing agent is a citrate salt.

51. A method according to claim 50 when the citrate salt is trisodium citrate.

52. A method according to claim 1 wherein the aminoglycoside is neomycin or a pharmaceutically acceptable salt thereof.

53. An anti-inflammatory pharmaceutical composition in a form suitable for topical administration to the eye which comprises an anti-inflammatory effective amount of a compound of the formula (I):

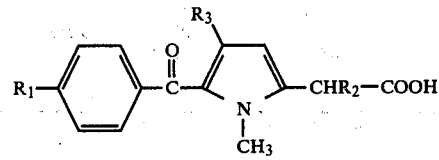

or a pharmaceutically acceptable salt thereof wherein $R_1$ is chloro or methyl; $R_1$ is hydrogen or methyl; and $R_3$ is hydrogen or methyl and an antibacterially effective amount of an aminoglycoside selected from the group consisting of neomycin, gentamycin, framycetin, polymixin B, tobramycin, kanamycin, vancomycin and amikacin, or a pharmaceutically acceptable salt thereof, in combination with an ocularly acceptable carrier.

54. A composition according to claim 53 which contains from 0.1 to 10% wt/wt of said compound in the form of a pharmaceutically acceptable salt.

55. A composition according to claim 53 which contains from 0.4 to 7% wt/wt of said compound in the form of a pharmaceutically acceptable salt.

56. A composition according to claim 53 which contains from 0.5 to 5% wt/wt of said compound in the form of a pharmaceutically acceptable salt.

57. A composition according to claim 53 which contains from 1 to 2% wt/wt of said compound in the form of a pharmaceutically acceptable salt.

58. A composition according to claim 53 which contains from 2 to 5% wt/wt of said compound in the form of a pharmaceutically acceptable salt.

59. A composition according to claim 53 which contains 2% wt of said compound in the form of a pharmaceutically acceptable salt.

60. A composition according to claim 53 which contains 5% wt of said compound in the form of a pharmaceutically acceptable salt.

61. A composition according to claim 53 which has been rendered substantially isotonic.

62. A composition according to claim 53 which contains from 0.01 to 2.5% of an antioxidant.

63. A composition according to claim 53 which contains from 0.05 to 2% of an antioxidant.

64. A composition according to claim 53 which contains from 0.5 to 1.5% of an antioxidant.

65. A composition according to claim 53 which contains 1% of an antioxidant.

66. A composition according to claim 62 wherein the antioxidant is a citrate salt, N-acetylcysteine, sodium thiosulphate, sodium metabisulphate or thiourea.

67. A composition according to claim 66 wherein the antioxidant is a citrate salt.

68. A composition according to claim 67 wherein the citrate salt is tri-sodium citrate.

69. A composition according to claim 53 which contains from 0.001 to 2% of a metal ion sequestering agent.

70. A composition according to claim 53 which contains from 0.5 to 1.5% of a metal ion sequestering agent.

71. A composition according to claim 69 which also contains from 0.01 to 2.5% of an antioxidant.

72. A composition according to claim 71 wherein the antioxidant and the metal ion sequestering agent is trisodium citrate.

73. A composition according to claim 53 wherein the pH of the composition is 6.0 to 8.6.

74. A composition according to claim 53 which contains a preservative.

75. A composition according to claim 74 wherein the preservative is phenylethanol and thiomersal.

76. A composition according to claim 75 which contains from 0.1 to 1% phenylethanol and from 0.001 to 0.025% thiomersal.

77. A composition according to claim 53 wherein the compound is the sodium or potassium salt of tolemetin.

78. A composition according to claim 53 wherein the compound is the sodium salt of tolemetin.

79. A composition according to claim 78 wherein the composition is in the form of a clear, sterile aqueous solution.

80. A composition according to claim 53 in the form of a sterile ointment.

81. A composition according to claim 53 in the form of a sterile emulsion.

82. A composition according to claim 53 in the form of a clear, sterile aqueous solution which comprises 0.5 to 2% wt/wt of the sodium salt of tolmetin, 0.1% to 3% of an aminoglycoside selected from the group consisting of neomycin, gentamycin, framycetin, polymixin B, tobramycin, kanamycin, vancomycin and amikacin or a pharmaceutically acceptable salt thereof, 0.5% to 2% of an antioxidant or sequestering agent and a preservative, the pH of said solution being 7.0 to 8.0.

83. A composition according to claim 82 wherein the antioxidant or sequestering agent is a citrate salt.

84. A composition according to claim 83 wherein the citrate salt is trisodium citrate.

85. A composition according to claim 84 wherein the preservative is a mixture of 0.5% phenylethanol and 0.01% thiomersal.

86. A composition according to claim 53 when the aminoglycoside or pharmaceutically acceptable salt thereof is present in an amount of from 0.1% to 3.0%.

87. A composition according to claim 53 when the aminoglycoside or pharmaceutically acceptable salt thereof is present in an amount of from 0.2% to 1%.

88. A composition according to claim 53 when the aminoglycoside or pharmaceutically acceptable salt thereof is present in an amount of 0.5%.

89. A composition according to claim 53 wherein the aminoglycoside is neomycin or a sulphate salt thereof.

90. A composition according to claim 89 which contains an amount of a solubilizing agent sufficient to prevent the neomycin cation from forming an insoluble precipitate with the anion of the compound of the formula (I).

91. A composition according to claim 90 wherein the solubilizing agent contains an anion selected from the group consisting of phosphate, citrate, glycerophosphate, sulphate, tartrate and borate.

92. A composition according to claim 90 wherein the compound of the formula (I) is in the form of the sodium salt of tolmetin, the aminoglycoside is neomycin or neomycin sulphate and the composition contains an amount of orthophosphate anion sufficient to prevent the neomycin cation from forming an insoluble precipitate with the tolmetin anion.

93. A composition according to claim 92 wherein the orthophosphate anion is present in the form of disodium hydrogen orthophosphate or dipotassium hydrogen orthophosphate.

94. A composition according to claim 91 wherein the weight ratio of solubilizing anion to neomycin sulphate is from 1:1 to 8:1.

95. A composition according to claim 91 wherein the weight ratio of solubilizing anion to neomycin sulphate is from 2:1 to 3:1.

96. A composition according to claim 90 wherein the solubilizing agent is polyvinyl pyrrolidone.

97. A composition according to claim 96 wherein the polyvinyl pyrrolidone is present in an amount of from 1 to 20% by weight.

98. A composition according to claim 96 wherein the polyvinyl pyrrolidone is present in an amount of from 5 to 15% by weight.

99. A composition according to claim 53 which comprises from 0.4% to 7% of the sodium salt of tolmetin, from 0.2% to 1% of neomycin sulphate, from 0.05 to 2% trisodium citrate, from 0.1 to 1% phenyl ethanol, and from 0.001 to 0.025% thiomersal in an aqueous solution at a pH of from 7.0 to 8.0.

100. A composition according to claim 53 which comprises from 2 to 5% of the sodium salt of tolmetin, 0.5% neomycin sulphate, 1 to 2% trisodium citrate, 0.5% phenyl ethanol, and 0.01% thiomersal in an aqueous solution at a pH of 7.5.

101. A composition according to claim 53 which comprises from 2 to 5% of the sodium salt of tolmetin, 0.5% neomycin sulphate, 10% polyvinyl pyrrolidone, 0.5% phenylethanol and 0.01% thiomersal in an aqueous solution having a pH of 7.5.

102. A composition according to claim 90 wherein the solubilizing agent is a citrate salt.

103. A composition according to claim 102 when the citrate salt is trisodium citrate.

104. A composition according to claim 53 wherein the aminoglycoside is neomycin or a pharmaceutically acceptable salt thereof.

* * * * *